(12) United States Patent
Norman

(10) Patent No.: US 10,342,631 B1
(45) Date of Patent: Jul. 9, 2019

(54) SHIELD FOR RECURRENT LARYNGEAL NERVE AND ASSOCIATED METHOD OF USE

(71) Applicant: James Glenn Norman, Tampa, FL (US)

(72) Inventor: James Glenn Norman, Tampa, FL (US)

( * ) Notice: Subject to any disclaimer, the term of this patent is extended or adjusted under 35 U.S.C. 154(b) by 0 days.

(21) Appl. No.: 16/219,038

(22) Filed: Dec. 13, 2018

(51) Int. Cl.
*A61B 90/00* (2016.01)
*A61B 90/35* (2016.01)
*A61B 46/20* (2016.01)
*A61B 5/00* (2006.01)

(52) U.S. Cl.
CPC ............ *A61B 90/04* (2016.02); *A61B 5/4893* (2013.01); *A61B 90/08* (2016.02); *A61B 2090/0436* (2016.02)

(58) Field of Classification Search
CPC ............ A61B 90/04; A61B 2017/0464; A61B 17/1128; A61K 35/12; A61K 35/51
See application file for complete search history.

(56) References Cited

U.S. PATENT DOCUMENTS

2004/0181240 A1* 9/2004 Tseng .................... A61F 9/0017 606/119

OTHER PUBLICATIONS

"The Pursuit of Regenerative Healing", date unknown, retrieved from https://amnioxmedical.com/human-amniotic-membrane/, 4 pages.
Actishield Amniotic Barrier Membrane, date unknown, retrieved from http://www.wright.com/products-biologics/actishield, 2 pages.
Allen et al., "Augmented Dried Versus Cryopreserved Amniotic Membrane as an Ocular Surface Dressing", PLOS One, 2013, 15 pages, vol. 8, No. 10.
Amnioexcel, Derma Sciences, date unknown, retrieved from http://www.dermasciences.com/amnioexcel, 4 pages.
AmnioGraft, Biotissue, date unknown, retrieved from http://www.biotissue.com/products/amniograft.aspx, 2 pages.
Avtec Surgical online catalog, SteriShield II Dual Layer Amnion Membrane (10mm x 25mm), date unknown, retrieved from https://www.bonegrafting.com/dual-layer-amnion-membrane-81025, 2 pages.
Biovance Human Amniotic Membrane Allograft, date unknown, retrieved from https://www.woundsource.com/product/biovance-human-amniotic-membrane-allograft, 6 pages.
Deniwar et al, "Electrophysiological Neural Monitoring of the Laryngeal Nerves in Thyroid Surger: Review of the Current Literature", Gland Surgery, 2015, pp. 368-375, vol. 4, No. 5.
Joliat et al., "Recurrent Laryngeal Nerve Injury After Thyroid and Parathyroid Surgery", Medicine, 2017, 5 pages, vol. 96, No. 17.
Snyder et al., "Elucidating Mechanisms of Recurrent Laryngeal Nerve Injury During Thyroidectomy and Parathyroidectomy", Journal of American College of Surgeons, 2008, pp. 123-130, vol. 206.
Surgraft, Dehydrated Amniotic Membrane Sheet Biological Protective Covering to Aid in Wound Management, brochure, date unknown, 2 pages.

* cited by examiner

*Primary Examiner* — Christine H Matthews
*Assistant Examiner* — Joshua Daryl D Lannu
(74) *Attorney, Agent, or Firm* — Thompson Coburn LLP

(57) ABSTRACT

A method includes covering a portion of a recurrent laryngeal nerve of a subject with a shield including extraembryonic tissue. The covering occurs during a neck surgery of the subject.

22 Claims, 4 Drawing Sheets

SHIELD FOR RECURRENT LARYNGEAL NERVE AND ASSOCIATED METHOD OF USE

CROSS-REFERENCE TO RELATED APPLICATIONS

Not Applicable.

STATEMENT REGARDING FEDERALLY SPONSORED RESEARCH OR DEVELOPMENT

Not Applicable.

APPENDIX

Not Applicable.

BACKGROUND

During neck surgeries, such as surgeries on the thyroid, parathyroid, esophagus, trachea, larynx, pharynx, cervical spine, cervical lymph nodes, and carotid arteries, the recurrent laryngeal nerve is subject to damage. For example, the recurrent laryngeal nerve may be damaged as a result of trauma, desiccation, or the like. As the recurrent laryngeal nerve is typically exposed early in operations and is often the most superficial structure in the operative field, it is at risk for injury during the remainder of the operation and then during the healing phase where it remains the most superficial structure at the healing interface. Once exposed, the nerve is subject to damage from direct and indirect insults which occur during the natural course of operating and dissecting the adjacent tissues from touching, traction, stretching, friction, desiccation and even inadvertent trauma from surgical instruments. As the operative field is kept dry using suction devices or the like, the nerve is subject to damage from desiccation or the physical act of keeping the operative field dry using absorbent sponges and the use of suction apparatus. Once exposed it is also highly subject to injury from thermal or electric injury from cautery devices used in nearby tissues. Such damage adversely affects patients as the recurrent laryngeal nerve is required for phonation and speech. Patients who incur damage to the recurrent laryngeal nerve may lose their voice for a minimum of 10-12 weeks and approximately 8-10% of patients may have a permanent injury that does not improve. Patients with an injured recurrent laryngeal nerve cannot talk normally. They can speak only in a whisper. Patients with an injured recurrent laryngeal nerve also frequently aspirate liquids as they cannot adequately protect their trachea from food/liquids entering their trachea.

Injury to the recurrent laryngeal nerve is known to occur in a significant percentage of head and neck operations. To mitigate or reduce the chance of injury to the recurrent laryngeal nerve, many maneuvers are undertaken by surgeons, but to date, there has been no decrease to this risk.

SUMMARY

An aspect of the disclosure is a method comprising covering a portion of a recurrent laryngeal nerve of a subject with a shield comprising extraembryonic tissue. The covering occurs during a neck surgery of the subject.

Another aspect of the disclosure is a method comprising exposing a recurrent laryngeal nerve of a subject during a neck surgery of the subject, and covering a portion of the exposed recurrent laryngeal nerve with a shield comprising amniotic tissue.

Still another aspect of the disclosure is a shield for protecting a recurrent laryngeal nerve of a subject during a surgical procedure. The shield comprises a layer of extraembryonic tissue having a first end edge, a second end edge, a first end margin adjacent the first end edge, a second end margin adjacent the second end edge, an intermediate region between the first and second end margins, a first curved side edge extending between the first and second end edges, and a second curved side edge extending between the first and second end edges. The shield diverges away from the first end edge and toward the second end edge.

Still another aspect of the disclosure is a method comprising covering a portion of a recurrent laryngeal nerve of a subject with a shield comprising biologic tissue, wherein the neck surgery comprises performing a procedure on the subject after covering the portion of the recurrent laryngeal nerve with the shield. The procedure comprises performing surgery on one or more of a thyroid, parathyroid, esophagus, trachea, larynx, pharynx, cervical spine, cervical lymph node, or carotid artery.

These are merely some of the innumerable aspects of the present disclosure and should not be deemed an all-inclusive listing of the innumerable aspects associated with the present disclosure. These and other aspects will become apparent to those skilled in the art in light of the following disclosure and accompanying drawings. The description and specific examples in this summary are intended for purposes of illustration only and are not intended to limit the scope of the present disclosure.

BRIEF DESCRIPTION OF THE DRAWINGS

The accompanying drawings, which are incorporated in and form a part of the specification, illustrate the embodiments of the present disclosure and together with the description, serve to explain the principles of the disclosure.

Figure 1:
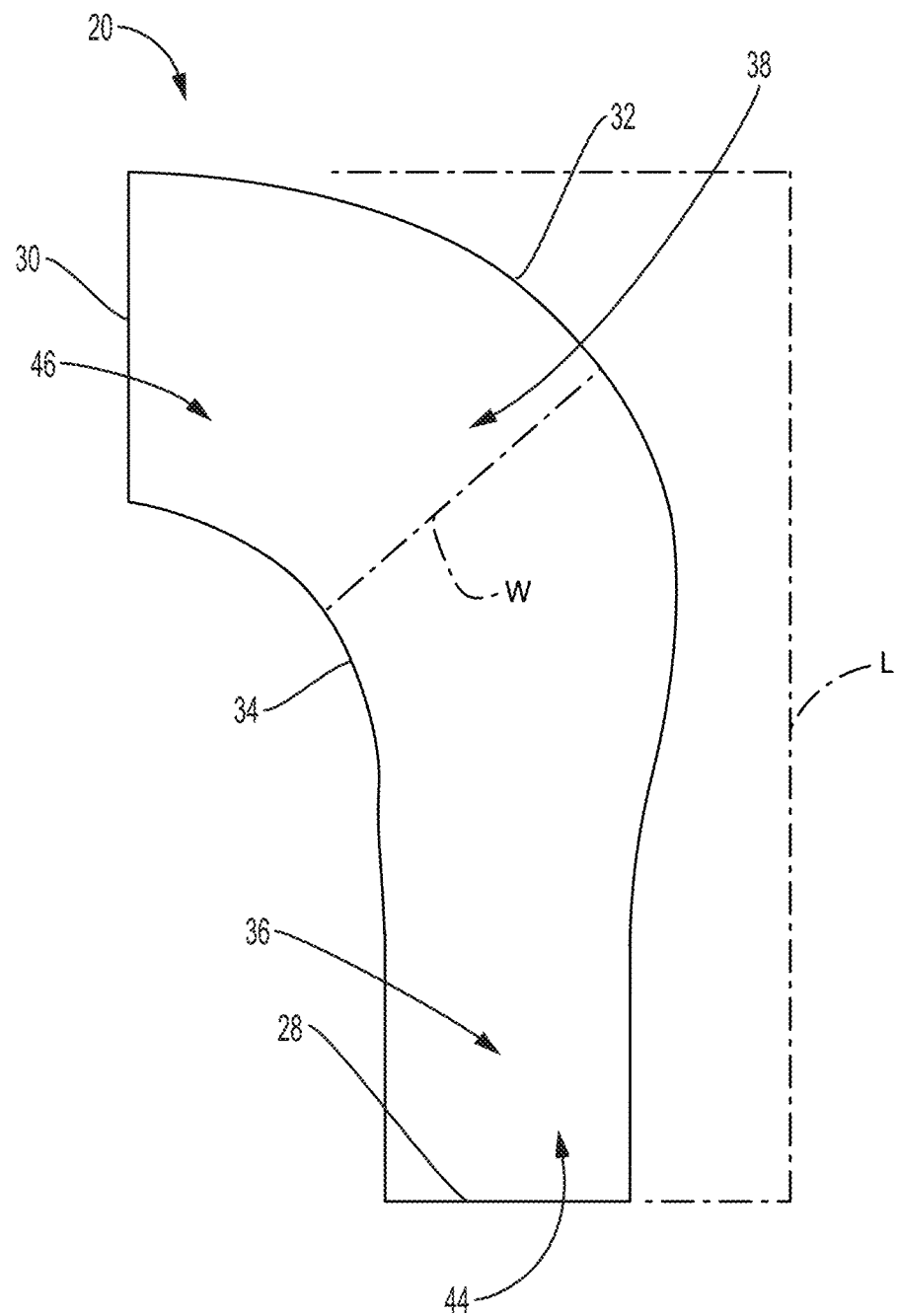
FIG. 1 illustrates a schematic top down view of one embodiment of a shield for a recurrent laryngeal nerve.

Reference characters in the written specification indicate corresponding items shown throughout the drawing figures.

DETAILED DESCRIPTION

Figure 3:
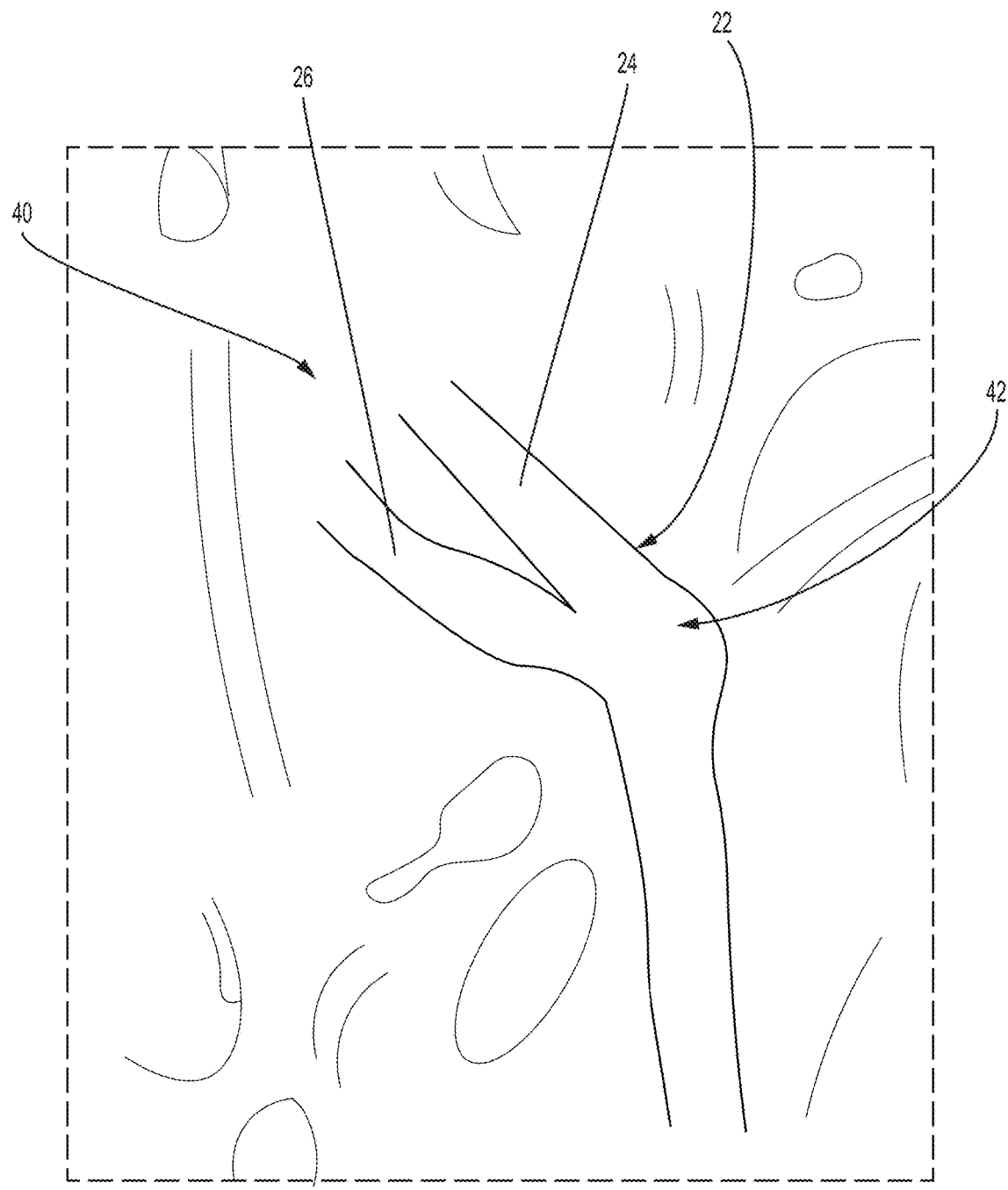
FIG. 3 illustrates a schematic view of a thyroid and exposed recurrent laryngeal nerve.
Figure 4:
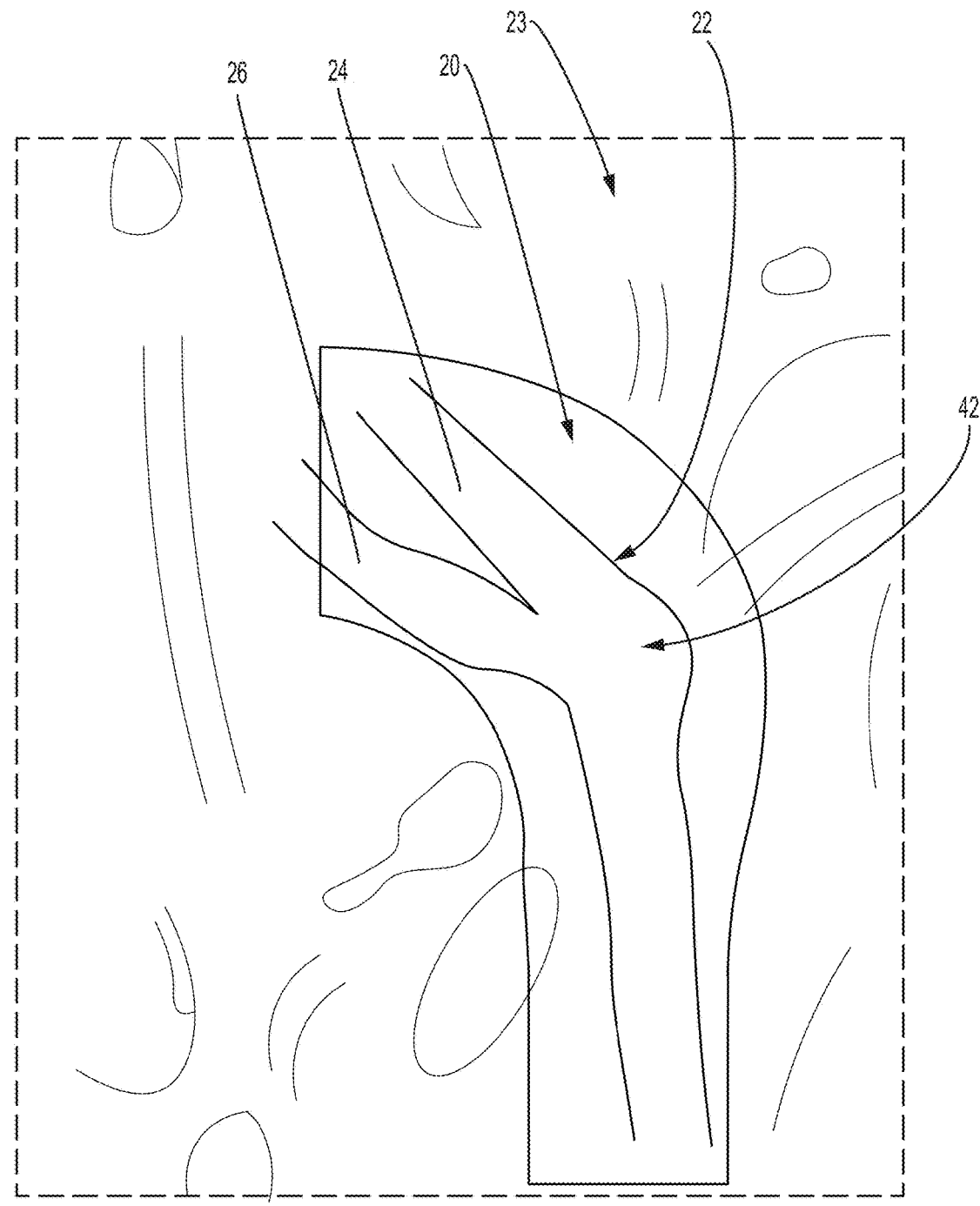
FIG. 4 illustrates a schematic view of the shield of FIG. 1 as applied to the recurrent laryngeal nerve of FIG. 3.

Referring to FIGS. 1, 3, and 4, a shield 20 for protecting a recurrent laryngeal nerve 22 is shown according to one embodiment. The shield 20 is shaped to correspond to the shape and structure of the recurrent laryngeal nerve 22 (e.g., adjacent the thyroid 23). The shape of the shield 20 accommodates the branching of the recurrent laryngeal nerve 22 into an external branch 24 and an internal branch 26. The shape of the shield 20 permits the recurrent laryngeal nerve 22 to maintain its normal, pre-surgical shape while being protected by the shield 20. This shape of the shield 20 negates the need to straighten or otherwise manipulate the recurrent laryngeal nerve 22 to cover it with the shield. This is advantageous because manipulating the recurrent laryngeal nerve 22 may damage the nerve and/or cause scarring.

The shaped nature of the shield 20 may provide a further advantage in that the shield need not be shaped to fit the recurrent laryngeal nerve 22. For example, the shield 20 may be of a material that is fragile and susceptible to tearing, bunching, or the like. A rectangular, square, or other such shape that is not tailored to the recurrent laryngeal nerve may bunch up during application over the recurrent laryngeal nerve complicating positioning. The shield may bunch up and adhere to itself such that the shield cannot cover the recurrent laryngeal nerve.

In some embodiments, the shield 20 comprises extraembryonic tissue. For example, the shield 20 may be entirely or partially of human amniotic tissue. The shield 20 may be of commercially available amniotic tissue such as Surgraft® Dehydrated Amniotic Sheet, BIOVANCE® Human Amnitoci Membrane Allograft, AMNIOEXCEL® Amniotic Allograft Membrane, Biotissue® AmnioGraft®, AMNIOX® amniotic membrane products, or Wright™ ACTISHIELD™. In alternative embodiments, the shield is of one or more of human amniotic tissue, human chorionic tissue, animal amniotic tissue, or animal chorionic tissue. For example, the shield 20 may comprise a combination of human amniotic tissue and human chorionic tissue.

In still a further alternative embodiment, the shield 20 is of biologic tissue suitable for protecting the recurrent laryngeal nerve 22. The biologic tissue may have one or more of the following characteristics: (1) man-made biologic; (2) surface roughness (e.g., mean roughness Ra or root mean square roughness RMS) of not more than 200% greater than that of suitable human amniotic tissue, and more preferably of not more than 50% greater than that of suitable human amniotic tissue, and even more preferably of not more than 25% greater than that of suitable human amniotic tissue (where suitable human amniotic tissue constitutes any of the following commercially available products: Surgraft® Dehydrated Amniotic Sheet, BIOVANCE® Human Amnitoci Membrane Allograft, AMNIOEXCEL® Amniotic Allograft Membrane, Biotissue® AmnioGraft®, AMNIOX® amniotic membrane products, and Wright™ ACTISHIELD™); (3) dissolvable or absorbable within a few days; (4) thin (e.g., have a thickness such that the tissue is translucent or transparent); (5) malleable; (6) transparent; (7) translucent; (8) non-inflammatory; (9) non-immunogenic such that it poses little if any risk of foreign body reaction; and (10) flexible such that the tissue takes on the shape of surrounding tissue (e.g., the tissue retains the general curved shape but is sufficiently flexible to conform to the tissues on which the tissue lays). In still further embodiments, the shield 20 comprises a combination of biologic tissue and other tissue (e.g., human amniotic tissue, human chorionic tissue, animal amniotic tissue, and/or animal chorionic tissue).

The shield 20 may comprise compounds and/or materials to assist in protection of the recurrent laryngeal nerve 22 and/or assist in healing of the recurrent laryngeal nerve and/or surrounding tissues following the procedure. For example, and without limitation, the shield may comprise an extracellular Matrix (ECM), growth factors, fibronectin, proteoglycans, laminin, and/or other proteins. The shield 20 may downregulate TGF-B, inhibit MMP's, suppress inflammatory cytokines, and decrease fibroblast formation.

Regardless of material, the shield 20 is typically cut from a sheet of the material before it is provided to a surgeon. This allows a surgeon to use the shield 20 without cutting out the shield from a sheet which takes time and can be difficult to do without damaging the material. The shield 20 may be cut from a sheet of material during a manufacturing process using a die cutting system or the like. This provides for more accurate shaping and a reduction in damage to the shield material in comparison to other techniques such as using scissors or a scalpel to cut the shape of the shield. Typically, the sheet will be of a relatively uniform thickness resulting in a shield 20 having a relatively uniform thickness. For example, and without limitation, the thickness of the shield 20 does not deviate at any one point more than 20% from the average thickness of the shield.

The shield 20 protects the recurrent laryngeal nerve 22 from rubbing and/or friction. The shield 20 further protects the recurrent laryngeal nerve 22 from desiccation by covering the nerve. The shield 20 further protects the recurrent laryngeal nerve 22 from electrical injury from instruments by providing an insulating layer and/or alternative electrical path. The shield 20 still further protects the recurrent laryngeal nerve 22 from bacteria or other pathogens by serving as a barrier when applied. When constructed of amnion, the shield 20 may further have anti-bacterial properties in addition to forming a barrier.

As shown in FIGS. 1 and 4, the shape of the shield 20 includes several features to accommodate the recurrent laryngeal nerve 22 to provide at least the benefits described herein (e.g., being shaped to match the recurrent laryngeal nerve 22 such that the shield's dimensions need not be modified before being applied to the recurrent laryngeal nerve 22). The shield 20 includes a first end edge 28 and a second end edge 30 opposite the first end edge 28. The shield 20 diverges away from the first end edge 28 and toward the second end edge 30. A first curved side edge 32 extends between the first 28 and second 30 end edges, and a second curved side edge 34 extends between the first 28 and second 30 end edges. Resulting from the divergence, the shield 20 includes a narrow region 36 and a flared region 38. The narrow region 36 is narrower than the flared region 38. The second end edge 30 of the flared region extends adjacent the larynx 40 of the subject when the shield is applied to the recurrent laryngeal nerve 22. The external 24 and internal 26 branches of the recurrent laryngeal nerve 22 enter the larynx 40, and the second end edge 30 and the shield 20 are shaped such that the second end edge 30 is adjacent the larynx 24 and the flared region 38 covers the branching of the recurrent laryngeal nerve 22. The curvature of each of the first and second curved side edges 32, 34 follows the curvature of the upper aspect 42 of the recurrent laryngeal nerve 22.

The shield 20 has a length L of between 3.5 centimeters and 4.5 centimeters, inclusive. In some embodiments, the length L is approximately 4 centimeters. In some embodiments, the shield 20 has a maximum width W of between 0.5 centimeters and 1.5 centimeters, inclusive. In some embodiments, the maximum width W is approximately 1 centimeter. The shield 20 is sized to overlay and cover the recurrent laryngeal nerve 22. In some embodiments, the shield 20 is sized such that the shield 20 overlays either side of recurrent laryngeal nerve 22 by approximately 2-4 millimeters. The overlay allows the shield 20 to adhere to the underlying tissues as a result of water surface tension and to move with the recurrent laryngeal nerve 22 rather than move across or separately from the underlying tissues.

It should be noted that ideally the shield 20 is reversible such that the shield 20 may be applied to either a right or a left recurrent laryngeal nerve 22. The shield 20 may be flipped over as needed to align with either nerve. Alternatively, the shield 20 may be available in a right or left version.

Figure 2:
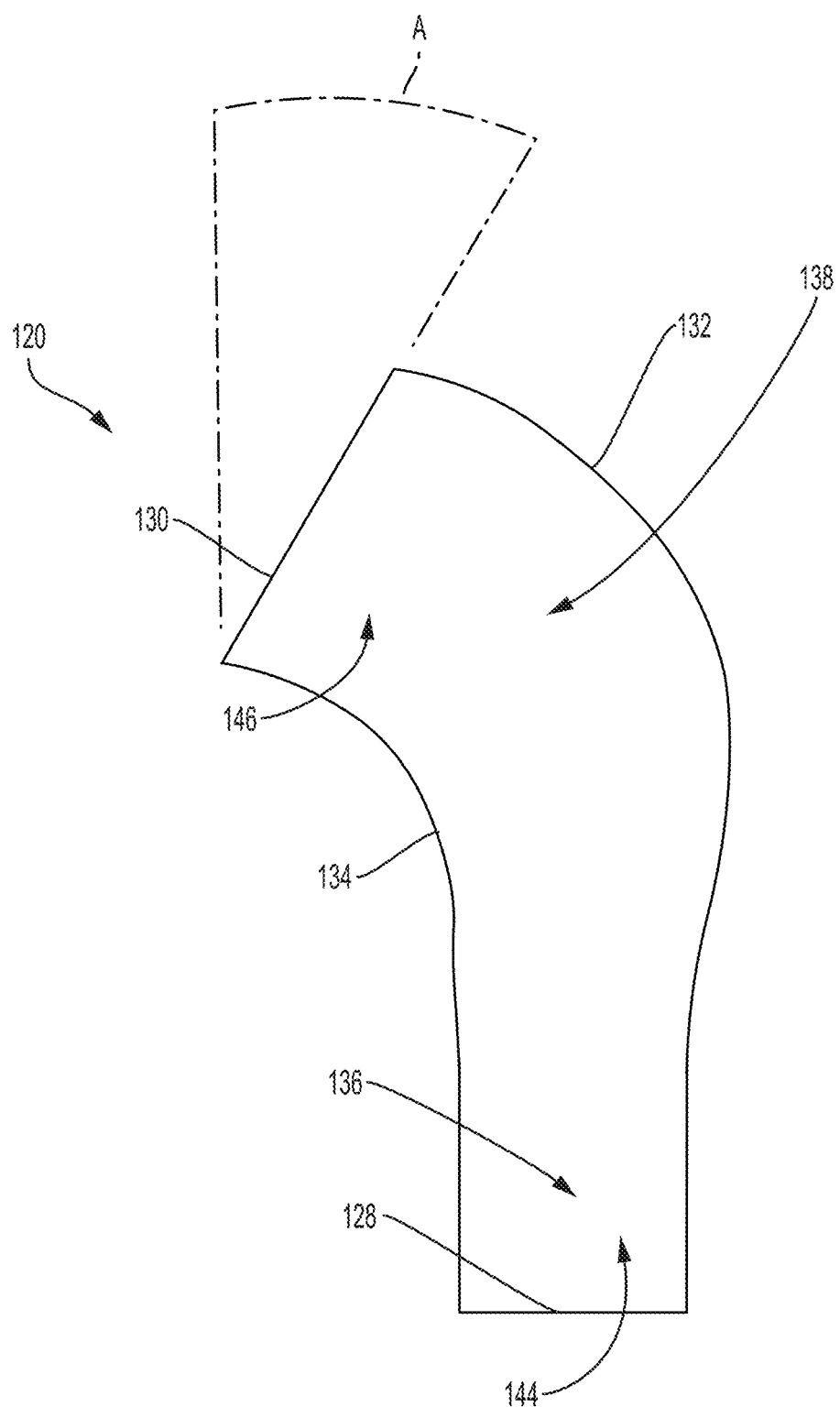
FIG. 2 illustrates a schematic top down view of an alternative embodiment of a shield for a recurrent laryngeal nerve.

Referring now to FIG. 2, an alternative embodiment of a shield 120 is shown. The shield 120 is similar to or the same as the shield 20 discussed with reference to FIG. 1 with like part numbers referring to like features (e.g., the first end edge 28 is the same as the first end edge 128). The shield 120 includes a second end edge 130 that extends along a 30 degree angle A that corresponds to the typical angle of the recurrent laryngeal nerve 22 as it enters the larynx 40.

Referring to FIG. 4, the shield 20 or 120 is used in covering a portion of the recurrent laryngeal nerve 22 of a subject. Advantageously, the shield 20 is provided pre-cut to the surgeon for use in protecting the recurrent laryngeal nerve such that the handling of the shield is reduced. In some embodiments, the shield 20 is provided to a surgeon as a part of a kit for use with a procedure of the type described herein. In one embodiment, the kit includes the shield 20 for covering the recurrent laryngeal nerve and a cotton tip swab for applying the shield. The cotton tip swab be treated or otherwise pre-prepared to be adapted for use with the shield. For example, the cotton tip swab may be a sterilized cotton tip swab.

The covering of the recurrent laryngeal nerve occurs during a neck surgery. The neck surgery comprises performing a procedure on the subject after covering the portion of the recurrent laryngeal nerve with the shield. The procedure comprises performing surgery on one or more of a thyroid, parathyroid, esophagus, trachea, larynx, pharynx, cervical spine, cervical lymph node, or carotid artery. For example, during a thyroidectomy, the recurrent laryngeal nerve 22 is exposed. The shield 20 will typically be applied promptly after exposure of the recurrent laryngeal nerve 22. This protects the recurrent laryngeal nerve 22 during the remainder of the thyroidectomy and the completion of the neck surgery. In this example, the remainder of the thyroidectomy constitutes the procedure. In some cases, the procedure may be prolonged, e.g., by a neck dissection to remove local lymph nodes. In such cases, the shield 20 protects the recurrent laryngeal nerve 22 throughout (e.g., prevents desiccation and decreases the likeliness of electrical injury or direct instrument trauma during a prolonged procedure). The surgeon refrains from removing the shield 20 from the recurrent laryngeal nerve 22 during the neck surgery and the shield 20 is left in the subject post-surgery.

During the procedure, such as the remainder of the thyroidectomy or any of the other procedures, the surgeon refrains from moving the shield 20 relative to the recurrent laryngeal nerve 22. When placing the shield 20 over the recurrent laryngeal nerve 22, the flared region 38 overlays the external and internal branches 24, 26 of the recurrent laryngeal nerve 22. The narrow region 36 covers a portion of the recurrent laryngeal nerve 22 prior to the branching. The second end edge 30 of the shield 20 extends adjacent the larynx 40. The recurrent laryngeal nerve 22 is in its pre-surgical shape upon being covered. In other words, the recurrent laryngeal nerve 22 is not reshaped (e.g., straightened) before being covered by the shield 20. The shape of the shield 20 also facilitates the placement of the shield 20 while avoiding creases or folds in the shield 20. Further, when placing the shield 20 over the recurrent laryngeal nerve 22, the first curved side 32 and the second curved side 34 follows the curvature of the curved upper aspect of the recurrent laryngeal nerve 22.

In an example of placing the shield 20, a first end margin 44 of the shield 20 is grasped and a second end margin 46 of the shield 20 is grasped. The shield 20 is oriented relative to the recurrent laryngeal nerve 22 such that the second end edge 30 of the shield 20 is adjacent the larynx 40 of the subject and such that the curvature of each of the first 32 and second 34 side edges corresponds to the curvature of the curved upper aspect of the recurrent laryngeal nerve 22. The shield 20 is brought into contact with the recurrent laryngeal nerve 22 such that a portion of the shield 20 contacts the nerve 22 while the grasping of at least one of the two end margins is maintained. For example, a cotton-tip swab is used to press an intermediate portion of the shield 20 to the recurrent laryngeal nerve 22. Next, the grasp on at least one of the two end margins is released. For example, the shield 20 is applied from the intermediate portion outward toward the two opposite ends.

After the recurrent laryngeal nerve 22 is covered, at least partially, by the shield 20, surgery procedure is performed (e.g., the removal of the thyroid in a thyroidectomy) by the surgeon. This allows the shield 20 to protect the recurrent laryngeal nerve 20 throughout the procedure and during any other portion of the operation (e.g., such as a neck dissection for lymph node removal) and/or after the procedure is completed. As such, the shield 20 reduces the chances of damage to the recurrent laryngeal nerve 22 and/or other negative outcomes of the type described herein.

In some embodiments, the shield 20 is left in place at the conclusion of the operation to protect the exposed surface of the recurrent laryngeal nerve from the movement of muscles and other tissues which lay across the exposed surface of the recurrent laryngeal nerve which is subject to trauma from friction during movement of the neck during the healing process. The shield 20 may also prevent scar formation between the recurrent laryngeal nerve and overlying tissues which ordinarily would not be adjacent to the recurrent laryngeal nerve. At the conclusion of the operation, the recurrent laryngeal nerve is exposed and laying upon the top surface of underlying tissues. When the wound is closed, the tissues above are laid down on the recurrent laryngeal nerve and thus the recurrent laryngeal nerve is exposed within the interface of the two tissue bodies. In such a situation, movement of the patient's neck (even minor movement) causes the recurrent laryngeal nerve to be rubbed on and traumatized by the overlying muscles and tissues. This can cause injuries to the recurrent laryngeal nerve during the first 24 hours after the procedure until the tissues begin to stick together and no longer slide relative to each other at the interface between the underlying and overlying tissues. The shield 20 minimizes or prevents such rubbing and may reduce or prevent such injuries.

Although discussed with respect to certain exemplary operations herein, the shield 20 is suitable for use during any operation in which the recurrent laryngeal nerve is exposed. For example, other procedures may include anterior cervical spine fusion, Carotid endarterectomy, central neck dissection for lymph nodes and or cancers of various types, cricopharyngeal myotomy, esophagectomy (cervical approach), excision of Zenker's diverticulum, hem ithyroidectomy or other partial thyroidectomy, lateral neck dissection for lymph nodes and/or cancer of various types, modified radical neck dissection (or radical neck dissection), neck biopsy, parathyroidectomy of all forms, partial laryngectomy, substernal goiter resection, and thyroidectomy partial or total.

In view of the foregoing, it will be seen that the several advantages of the disclosure are achieved and attained.

The embodiments were chosen and described in order to best explain the principles of the disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method comprising:
performing a neck surgery on a subject;
during the neck surgery, covering a portion of a recurrent laryngeal nerve of the subject with a shield comprising extraembryonic tissue.

2. The method as set forth in claim 1 wherein the shield includes a flared region, and wherein covering a portion of the recurrent laryngeal nerve comprises covering portions of branches of the recurrent laryngeal nerve with the flared portion of the shield.

3. The method as set forth in claim 1 wherein the extraembryonic tissue comprises a layer of extraembryonic tissue.

4. The method as set forth in claim 1 wherein the shield constitutes a layer of extraembryonic tissue.

5. The method as set forth in claim 1 wherein the extraembryonic tissue comprises amniotic membrane tissue.

6. The method as set forth in claim 1 wherein the extraembryonic tissue comprises chorionic membrane tissue.

7. The method as set forth in claim 1 wherein the extraembryonic tissue comprises one or more of human amniotic tissue, human chorionic tissue, non-human amniotic tissue, or non-human chorionic tissue.

8. The method as set forth in claim 1 further comprising refraining from removing the shield from the recurrent laryngeal nerve during the neck surgery such that the shield is in the subject post-surgery.

9. The method as set forth in claim 1 wherein the neck surgery comprises performing a procedure on the subject after covering the portion of the recurrent laryngeal nerve with the shield, the procedure comprising performing surgery on one or more of a thyroid, parathyroid, esophagus, trachea, larynx, pharynx, cervical spine, cervical lymph node, or carotid artery.

10. The method as set forth in claim 9 further comprising refraining from moving the shield relative to the recurrent laryngeal nerve during the procedure.

11. The method as set forth in claim 9 wherein the recurrent laryngeal nerve comprises an external branch and an internal branch, wherein the shield includes a flared end region, and wherein the flared end region covers portions of the external and internal branches of the recurrent laryngeal nerve upon the covering of the portion of the recurrent laryngeal nerve with the shield.

12. The method as set forth in claim 9 wherein the shield includes a flared region having an edge, and wherein the edge of the flared region extends adjacent the larynx upon the covering of the portion of the recurrent laryngeal nerve with the shield.

13. The method as set forth in claim 9 wherein the recurrent laryngeal nerve includes an upper aspect, an external branch, and an internal branch, and the shield includes a flared region and a narrow region, the narrow region being narrower than the flared region, the flared region having an edge, and wherein the covering of the portion of the recurrent laryngeal nerve with the shield comprises:
covering a portion of the upper aspect of the recurrent laryngeal nerve with the narrower region of the shield; and
covering portions of the external and internal branches of the recurrent laryngeal nerve with the flared region of the shield in a manner such that the edge of the flared region extends adjacent the larynx of the subject.

14. The method as set forth in claim 13 wherein the covering is performed in a manner such that the recurrent laryngeal nerve is in a pre-surgical shape upon being covered.

15. The method as set forth in claim 13 further comprising refraining from reshaping the recurrent laryngeal nerve from a pre-surgical shape during the covering of the portion of the recurrent laryngeal nerve.

16. The method as set forth in claim 1 wherein the covering of the portion of the recurrent laryngeal nerve with the shield comprises covering the portion of the recurrent laryngeal nerve with the shield in a manner such that the shield is devoid of any creases or folds.

17. The method as set forth in claim 1 wherein:
the recurrent laryngeal nerve includes a curved upper aspect, an external branch, and an internal branch, the curved upper aspect having a curvature;
the shield comprises a first end edge, a second end edge, a first curved side edge extending between the first and second end edges, and a second curved side edge extending between the first and second end edges, the first curved side edge having a curvature, the second curved side having a curvature, the shield diverging away from the first end edge and toward the second end edge; and
the covering of the portion of the recurrent laryngeal nerve with the shield comprises aligning the shield with the recurrent laryngeal nerve such that the second end edge of the shield extends adjacent the larynx of the subject and the curvature of each of the first and second side edges follows the curvature of the curved upper aspect of the recurrent laryngeal nerve.

18. The method as set forth in claim 1 wherein the recurrent laryngeal nerve includes a curved upper aspect, an external branch, and an internal branch, wherein the curved upper aspect has a curvature, wherein the shield comprises a first end edge, a second end edge, a first end margin adjacent the first end edge, a second end margin adjacent the second end edge, an intermediate region between the first and second end margins, a first curved side edge extending between the first and second end edges, and a second curved side edge extending between the first and second end edges, the first curved side edge having a curvature, the second curved side edge having a curvature, the shield diverging away from the first end edge and toward the second end edge, and wherein the covering of the portion of the recurrent laryngeal nerve with the shield comprises:
grasping the first end margin of the shield;
grasping the second end margin of the shield;
orienting the shield relative to the recurrent laryngeal nerve such that the second end edge of the shield is adjacent a larynx of the subject and such that the curvature of each of the first and second side edges corresponds to the curvature of the curved upper aspect of the recurrent laryngeal nerve;
contacting the recurrent laryngeal nerve with a portion of the shield while maintaining grasping of at least one of the first and second end margins of the shield; releasing the grasp on the at least one of the first and second end margins of the shield after the portion contacts the recurrent laryngeal nerve, such that the shield overlies portions of the curved upper aspect and portions of the external and internal branches of the recurrent laryngeal nerve.

19. A method comprising:

exposing a recurrent laryngeal nerve of a subject; and covering a portion of the exposed recurrent laryngeal nerve with a shield comprising amniotic tissue.

20. The method as set forth in claim 19 further comprising performing a procedure on the subject while the portion of the recurrent laryngeal nerve is covered by the shield, the procedure comprising performing surgery on one or more of a thyroid, parathyroid, esophagus, trachea, larynx, pharynx, cervical spine, cervical lymph nodes, or carotid artery.

21. A method comprising:

exposing a recurrent laryngeal nerve of a subject;

covering a portion of the exposed recurrent laryngeal nerve with a shield comprising biologic tissue, the biologic tissue being not of the subject; and performing a procedure on the subject while the portion of the recurrent laryngeal nerve is covered by the shield, the procedure comprising performing surgery on one or more of a thyroid, parathyroid, esophagus, trachea, larynx, pharynx, cervical spine, cervical lymph nodes, or carotid artery.

22. A method in accordance with claim 21 wherein the biologic tissue is at least partially transparent such that the recurrent laryngeal nerve is visible when covered by the shield.

* * * * *